United States Patent
Han et al.

(10) Patent No.: US 11,185,618 B2
(45) Date of Patent: Nov. 30, 2021

(54) NEGATIVE PRESSURE GENERATING DEVICE AND AUTOMATIC NEGATIVE PRESSURE WOUND THERAPY DEVICE HAVING PRESSURE CHANGING FUNCTION USING THE SAME

(71) Applicant: INDUSTRY-UNIVERSITY COOPERATION FOUNDATION HANYANG UNIVERSITY, Seoul (KR)

(72) Inventors: Seog Young Han, Seoul (KR); Dae Hwan Moon, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 265 days.

(21) Appl. No.: 16/348,191

(22) PCT Filed: Nov. 8, 2017

(86) PCT No.: PCT/KR2017/012584
§ 371 (c)(1),
(2) Date: May 8, 2019

(87) PCT Pub. No.: WO2018/088791
PCT Pub. Date: May 17, 2018

(65) Prior Publication Data
US 2019/0275215 A1   Sep. 12, 2019

(30) Foreign Application Priority Data
Nov. 8, 2016 (KR) .................. 10-2016-0148159

(51) Int. Cl.
*A61M 1/00* (2006.01)
*F04B 53/14* (2006.01)
*F03G 1/00* (2006.01)

(52) U.S. Cl.
CPC ............ *A61M 1/0001* (2013.01); *A61M 1/00* (2013.01); *A61M 1/74* (2021.05);
(Continued)

(58) Field of Classification Search
CPC .... A61M 1/00; A61M 1/0001; A61M 1/0066; A61M 1/0068; A61M 1/0082;
(Continued)

(56) References Cited

U.S. PATENT DOCUMENTS 197,311 A * 11/1877 Badwin ................... F16H 19/06
                                                                74/89.22
467,054 A *  1/1892 Scharff ...................... B62B 9/08
                                                                188/20
(Continued)

FOREIGN PATENT DOCUMENTS

JP   2013-538083 A   10/2013
JP   5548454 B2   5/2014
(Continued)

OTHER PUBLICATIONS

KR Office Action for Application No. 10-2016-0148159 dated Jul. 19, 2018.
(Continued)

*Primary Examiner* — Nicholas J Weiss
*Assistant Examiner* — Seth Han
(74) *Attorney, Agent, or Firm* — Sughrue Mion, PLLC (57) ABSTRACT

The present invention relates to a negative pressure generating device and an automatic negative pressure wound therapy device having a pressure changing function using the same. The present invention includes a static load elastic
(Continued)

unit which provides an elastic force having a predetermined magnitude; a rotating unit which is connected to the static load elastic unit to rotate by the static load elastic unit; and a negative pressure cylinder which is connected to the rotating unit and interworks with the rotation of the rotating unit to generate a negative pressure therein. According to the present invention, a constant negative pressure may be consistently generated by a mechanical structure so that a manufacturing cost is significantly reduced as compared with an electrical structure and the size may be reduced.

8 Claims, 4 Drawing Sheets (52) U.S. Cl.
CPC ....... *A61M 2205/3334* (2013.01); *F03G 1/00* (2013.01); *F04B 53/14* (2013.01); *F04C 2220/10* (2013.01)

(58) Field of Classification Search
CPC ..... A61M 2205/8281; F04C 2/00; F04B 9/02; F04B 9/107; F04B 9/127; F04B 11/0033; F04B 17/02; F04B 7/061; F04B 35/00; F04D 13/028
USPC .......................................................... 92/137
See application file for complete search history.

(56) References Cited

U.S. PATENT DOCUMENTS

| | | | | |
|---|---|---|---|---|
| 828,624 | A * | 8/1906 | Mcintire | F15B 15/084 92/137 |
| 2,270,043 | A * | 1/1942 | Fourness | B65B 63/024 206/410 |
| 2,956,511 | A * | 10/1960 | Morehead | E03B 5/04 417/415 |
| 4,230,520 | A * | 10/1980 | Morgan | G11B 23/113 156/505 |
| 2009/0270843 | A1 | 10/2009 | Saxena et al. | |
| 2010/0042074 | A1* | 2/2010 | Weston | A61M 1/0068 604/543 |
| 2010/0262094 | A1* | 10/2010 | Walton | A61F 13/00068 604/319 |
| 2013/0018338 | A1 | 1/2013 | Weston et al. | |
| 2014/0163521 | A1 | 6/2014 | O'Connor | |
| 2014/0358097 | A1 | 12/2014 | Walton et al. | |
| 2015/0148761 | A1 | 5/2015 | Hu et al. | |
| 2016/0123447 | A1* | 5/2016 | Chen | E06B 9/322 160/168.1 P |

FOREIGN PATENT DOCUMENTS

| | | |
|---|---|---|
| JP | 5608745 B2 | 10/2014 |
| KR | 20-0293046 Y1 | 10/2002 |
| KR | 10-1360194 B1 | 2/2014 |

OTHER PUBLICATIONS

International Search Report for PCT/KR2017/012584 dated Feb. 14, 2018 [PCT/ISA/210].
Written Opinion dated Feb. 14, 2018 from the International Searching Authority in International Application No. PCT/KR2017/012584.
Notice of Allowance dated Jan. 16, 2019 from the Korean Intellectual Property Office in KR Application No. 10-2016-0148159.
Extended European Search Report dated May 8, 2020 from the European Patent Office in EP Application No. 17870523.2.

* cited by examiner

NEGATIVE PRESSURE GENERATING DEVICE AND AUTOMATIC NEGATIVE PRESSURE WOUND THERAPY DEVICE HAVING PRESSURE CHANGING FUNCTION USING THE SAME

CROSS REFERENCE TO RELATED APPLICATIONS

This application is a National Stage of International Application No. PCT/KR2017/012584, filed on Nov. 8, 2017, which claims priority from Korean Patent Application No. 10-2016-0148159, filed on Nov. 8, 2016.

TECHNICAL FIELD

The present invention relates to a negative pressure generating device and an automatic negative pressure wound therapy device having a pressure changing function, and more particularly, to a negative pressure generating device which is used for treatment, such as the discharge of blood or exudates at a surgical site, is easy to carry and includes a negative pressure changing function.

BACKGROUND ART

Unlike conventional dressings, which play a passive role by providing a wet environment to provide a wound therapy environment, the negative pressure wound therapy device (NPWT) actively promotes wound healing so that the usage of the negative pressure wound therapy device has been gradually increasing in recent years. Especially, in developed countries such as USA and Europe, the usage of vacuum negative pressure devices is increasing in recent years and products which reduce the risk of infection and are easy to carry are being developed.

A vacuum negative pressure device applies a negative pressure to a wounded site of a patient to suck exudates such as blood and oozing fluids and promote blood circulation of the wounded site to induce rapid wound healing. However, such a vacuum negative pressure device is configured by a foam dressing which covers the wound, a pump which generates a negative pressure, and a liquid tank which stores exudates so that the volume thereof is large. Therefore, there are problems in that it is difficult to carry the vacuum negative pressure device and it is not easy for the patient to be discharged from the hospital, and to move in daily life while using the vacuum negative pressure device.

Further, since the vacuum negative pressure device is an electrically powered device using an expensive component such as a pump operating by electricity, there is another problem in that it is not easy to use the vacuum negative pressure device in developing countries where medical conditions are insufficient. Further, since the vacuum negative pressure device is an expensive device, it may be considered to reuse the vacuum negative pressure device. However, in this case, there is a risk of infection.

It is possible to consider a mechanical vacuum negative pressure generating device which does not use the electricity. However, in the case of the mechanical type, it is difficult to consistently form a negative pressure with a constant magnitude and change the negative pressure.

As a related art, there is Japanese Laid-Open Publication No. 2013-538083 (entitled Controlled negative pressure device and alarm apparatus, published on Oct. 10, 2013).

DISCLOSURE

Technical Problem

The present invention has been made to solve the problems of the related art as described above and an object of the present invention is to provide a negative pressure generating device which is mechanically operated and consistently forms a negative pressure with a constant magnitude.

Another object of the present invention is to change a negative pressure in a negative pressure generating device which is mechanically operated.

Technical Solution

According to an aspect of the present invention, the present invention includes a static load elastic unit which provides an elastic force having a predetermined magnitude; a rotating unit which is connected to the static load elastic unit to rotate by the static load elastic unit; and a negative pressure cylinder which is connected to the rotating unit and interworks with the rotation of the rotating unit to generate a negative pressure therein.

The negative pressure cylinder includes: a cylinder housing; a piston which is linearly movably installed in the cylinder housing; and a connecting unit which connects the piston and the static load elastic unit.

An interlocking assembly is provided between the rotating unit and the negative pressure cylinder to connect to each other and the interlocking assembly is connected to the piston of the negative pressure cylinder to generate the negative pressure while pulling the piston by a torque of the rotating unit.

The interlocking assembly includes: a winder which winds a wire while rotating coaxially with the rotating unit; and a pulley which is installed to be adjacent to the winder and supports the wire or changes a movement path of the wire, one end of the wire is connected to the wire to be continuously wound and the other end is connected to the connecting unit of the negative pressure cylinder via the pulley to pull the piston.

A diameter of the rotating unit is larger than the winder of the interlocking assembly.

The rotating unit includes a negative pressure changing unit which interferes with the rotating unit to adjust a torque of the rotating unit.

In the negative pressure changing unit, an interfering protrusion which selectively locks gear teeth provided on an outer circumferential surface of the rotating unit to adjust a torque is provided to be movable to the outer circumferential surface of the rotating unit and the negative pressure changing unit includes an elastic member which elastically supports the interfering protrusion in the outer circumferential direction of the rotating unit.

The gear teeth provided on the outer circumferential surface of the rotating unit is continuously or discontinuously provided along the outer circumferential surface of the rotating unit to vary a rotating speed of the rotating unit.

A negative pressure tube which outwardly protrudes is exchangeably coupled to an inlet of the negative pressure cylinder.

The static load elastic unit is a constant torque spring which is configured such that a steel strip is wound around a drum.

According to another aspect of the present invention, the present invention includes: an external housing; and any one of the negative pressure generating devices described above installed in the external housing.

Advantageous Effects

The negative pressure generating device and the automatic negative pressure wound therapy device having a pressure changing function according to the present invention as described above have the following effects.

According to the present invention, a constant negative pressure may be consistently generated by a mechanical structure so that a manufacturing cost is significantly reduced as compared with an electrical structure and the size may be reduced.

Specifically, according to the present invention, the electricity is not used so that it is free from the usage environment and the device is portable so that the user may more easily use the device. Further, the risk of the bacterial infection may be significantly reduced through one-time use.

Further, according to the present invention, the negative pressure is adjusted to be periodically changed by interworking of a rotating unit and a negative pressure changing unit so that the wound site of the patient who uses this device may be quickly recovered.

DESCRIPTION OF MAIN REFERENCE NUMERALS OF DRAWINGS

10: External housing
11: Installation space
20: Static load elastic unit
21,23: First drum and Second drum
25: Steel strip
30: Rotating unit
35: Gear teeth
40: Interlocking assembly
43: Winder
45: Pulley
50: Negative pressure cylinder
55: Piston
58: Connecting unit
W: Wire

BEST MODE

Hereinafter, some embodiments of the present invention will be described in detail with reference to the accompanying drawings. When reference numerals denote components in the drawings, even though the like parts are illustrated in different drawings, it should be noted that like reference numerals refer to the same parts. In describing the embodiments of the present invention, when it is determined that the detailed description of the known art related to the present invention may obscure the gist of the present invention, the detailed description thereof will be omitted.

The present invention relates to a device for generating a negative pressure and an automatic negative pressure wound therapy device applying the same. The present invention may be used for various medical purposes such as general surgery, thoracic surgery, and neurosurgery as well as a negative pressure wound therapy device for improving blood flow. The negative pressure generating device according to the present invention may also be used for non-medical purpose.

Figure 1:
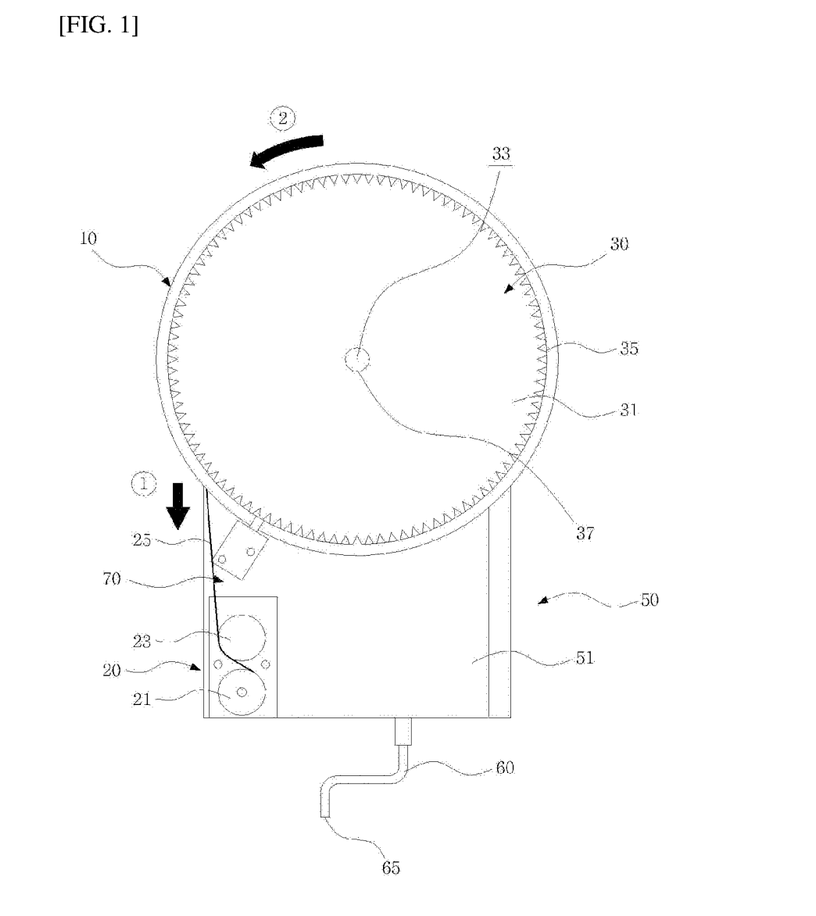
FIG. 1 is a plan view illustrating an internal structure by removing a cover from one exemplary embodiment of a negative pressure generating device according to the present invention.

A basic frame of the present invention is formed by an external housing 10. An installation space 11 is formed in the external housing 10 and is shielded by a cover. For reference, the cover is omitted to illustrate an internal structure. The external housing 10 may be formed of a light material such as synthetic resin. Referring to FIG. 1, an upper portion of the external housing 10 is formed to have a substantially circular shape and a lower portion is formed to have a rectangular shape, but the shape of the external housing 10 is not necessarily limited thereto.

A static load elastic unit 20 is provided in the installation space 11 of the external housing 10. The static load elastic unit 20 provides an elastic force having a predetermined magnitude to generate a constant negative pressure. In the present exemplary embodiment, the static load elastic unit 20 is a constant torque spring configured by winding a flexible steel strip 25 around a drum. The static load elastic unit 20 basically has a tendency to keep the steel strip 25 wound around the drum. When the steel strip 25 is installed to be unwound, the steel strip is gradually wound to operate a rotating unit 30 and a negative pressure cylinder 50 which will be described below. That is, the static load elastic unit 20 may also be considered as a spring motor.

In the present exemplary embodiment, the static load elastic unit 20, as illustrated in FIG. 1, may be configured by a first drum 21 and a second drum 23 which are rotatably installed and the steel strip 25 wound around the first drum and the second drum. One end of the steel strip 25 is connected to the rotating unit 30 and the other end is connected to the first drum 21 to rotate the rotating unit 30 while being wound by the elastic force. The static load elastic unit 20 may not be necessarily a single spring motor, but may be a multiple spring motor including a plurality of drums and steel strips 25.

The static load elastic unit 20 has a torque with a predetermined magnitude so that the static load elastic unit 20 may rotate the rotating unit 30 while being gradually wound. That is, as the winding degree of the steel strip 25 is increased, the elastic force of the static load elastic unit 20 is not reduced but an elastic force with a predetermined magnitude is provided so that, consequently, a constant negative pressure is generated.

The rotating unit 30 is provided in the installation space 11. The rotating unit 30 pulls a piston 55 in the negative pressure cylinder 50 while rotating around a rotary shaft 37 in the installation space 11. More specifically, the rotating unit 30 rotates by the steel strip 25 of the static load elastic unit 20 and transmits the torque to the piston 55 of the negative pressure cylinder 50 so that the piston 55 linearly moves to generate a negative pressure.

Figure 3:
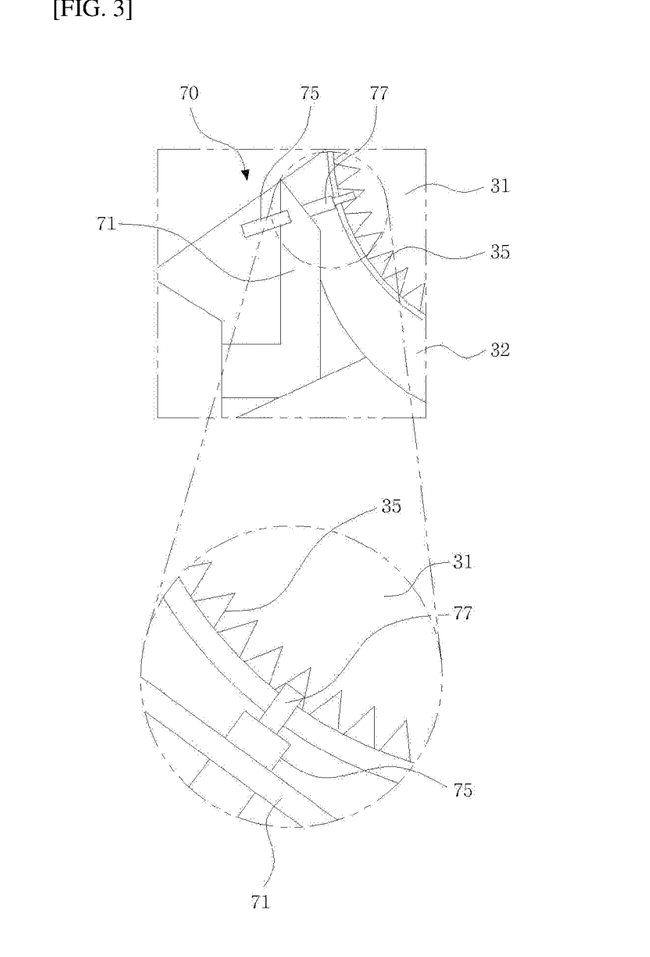
FIG. 3 is a perspective view enlarging major components of a rotating unit and a negative pressure changing unit which configure an exemplary embodiment of the present invention.

The rotating unit 30 has a thin disk shape. Referring to FIG. 3, a frame of the rotating unit 30 is formed by a rotary body 32 having a predetermined thickness. The end portion of the steel strip 25 of the static load elastic unit 20 is connected to the rotary body 32 so that the steel strip 25 may be wound or reversely unwound around an outer circumferential surface of the rotary body 32 to some content.

A gear plate 31 is provided above the rotary body 32. The gear plate 31 is coupled to the rotary body 32 to rotate together and gear teeth 35 are provided on an outer circumferential surface thereof. The gear teeth of the gear plate 31 are interfered by the negative pressure changing unit 70 which will be described below to apply a constant pressure, which is periodically repeated, to the rotating unit 30. Therefore, a force of the gear plate 31 that pulls the piston 55 of the negative pressure cylinder 50 is also changed at a predetermined interval and consequently, the negative pressure may vary. For reference, the gear plate 31 may be integrally formed with the rotary body 32.

In the exemplary embodiment, the gear teeth 35 formed on the gear plate 31 may be continuously and constantly formed around the outer circumferential surface of the gear plate 31. Therefore, the variable negative pressure is repeated at a predetermined interval. However, the gear teeth 35 may be discontinuously formed on the gear plate 31. For example, the gear teeth 35 are formed in a predetermined section of the outer circumferential surface of the gear plate 31, but the gear teeth 35 may be omitted in a predetermined section. Therefore, this pattern is repeated to increase the changing interval of the negative pressure. However, the negative pressure may vary by changing a pitch of the gear teeth 35.

In the meantime, a rotary hole 33 is formed in the rotating unit 30 and the rotary shaft 37 is fitted to the rotary hole 33 to serve as a rotation center of the rotating unit 30. The rotary shaft 37 also serves as a rotary shaft 37 of a winder 43 of an interworking assembly 40 which will be described below.

In the exemplary embodiment, the rotating unit 30 is not directly connected to the negative pressure cylinder 50, but is connected to the negative pressure cylinder 50 via the interworking assembly 40. The interworking assembly 40 is provided between the rotating unit 30 and the negative pressure cylinder 50 to connect to each other. The interworking assembly 40 is connected to the piston 55 of the negative pressure cylinder 50 to pull the piston 55 by the torque of the rotating unit 30 and generate the negative pressure.

Figure 2:
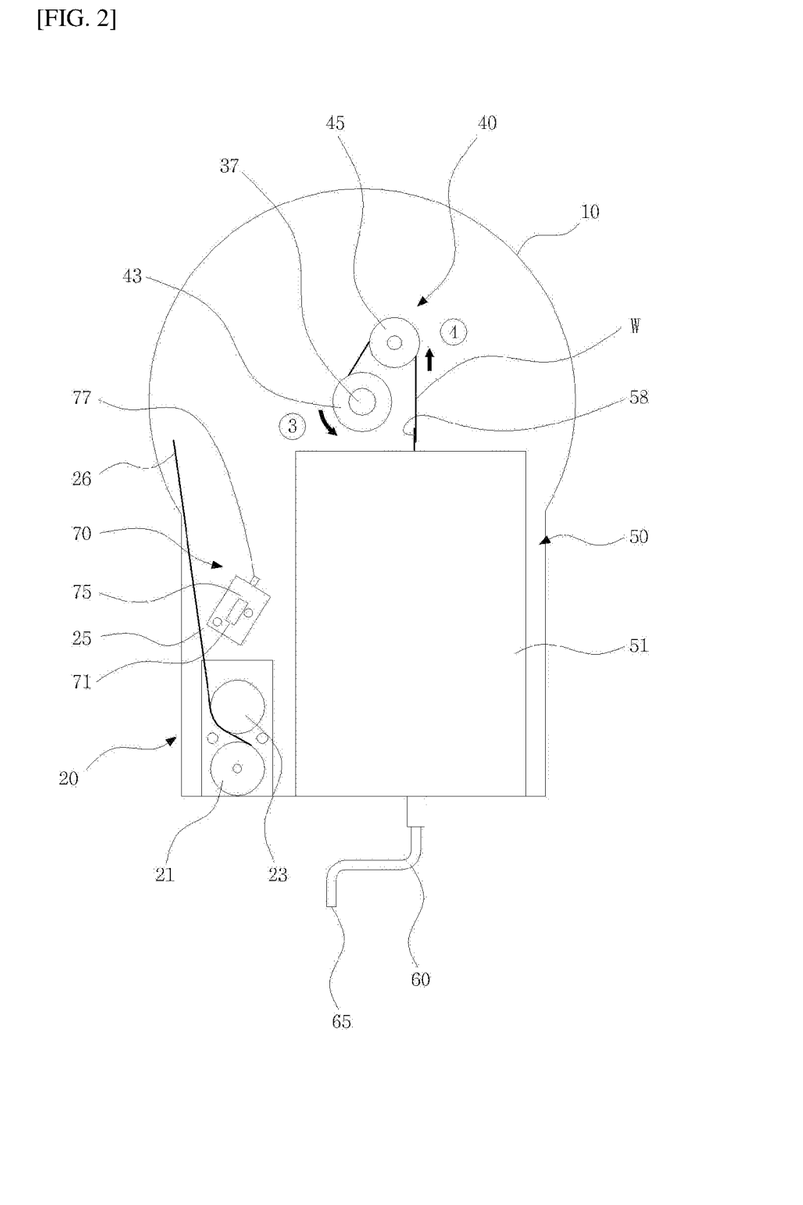
FIG. 2 is a plan view illustrating a state in which a rotating unit is removed from the exemplary embodiment illustrated in FIG. 1.

As illustrated in FIG. 2, the interworking assembly 40 mainly includes a winder 43 and a pulley 45. The winder 43 winds the wire W and rotates coaxially with the rotary shaft 37 of the rotating unit 30. One end of the wire W which is wound around the winder 43 is connected to the winder 43 so that when the winder 43 rotates, the wire W is continuously wound and the other end is connected to the connecting unit 58 of the negative pressure cylinder 50 via a pulley 45 to pull the piston 55.

The winder 43 has a disk shape which rotates around the rotary shaft 37 and the pulley 45 is installed to be adjacent to the winder 43 and functions to support the wire W or change a movement path of the wire W. That is, the pulley 45 is considered as an idler pulley. However, the pulley 45 may be omitted.

In this case, when sizes of the rotating unit 30 and the interworking assembly 40 are compared, a diameter of the rotating unit 30 is larger than the winder 43 of the interworking assembly 40. In the present exemplary embodiment, the diameter of the rotating unit 30 is at least five times or larger than a diameter of the winder 43. By doing this, an angle at which the rotating unit 30 rotates by the static load elastic unit 20 is reduced and a degree of pulling of the connecting unit 58 of the negative pressure cylinder 50 while the winder 43 rotates is reduced. By doing this, a length by which the connecting unit 58 of the negative pressure cylinder 50 is pulled is reduced and the negative pressure may be slowly generated for a long time. For example, since the diameter of the rotating unit 30 is very large, the rotating unit 30 may be limited to make one rotation in total, that is, 360 degrees by the static load elastic unit 20. Further, in this case, the winder 43 which coaxially rotates with the rotating unit 30 also rotates only at 360 degrees and during this process, the wire W wound on the outer surface of the winder 43 is shortened by a length to wrap the outer surface of the winder 43 once. As a result, the connecting unit 58 of the negative pressure cylinder 50 connected to the wire W is also pulled by a length to wrap the outer surface of the winder 43 once.

Figure 4:
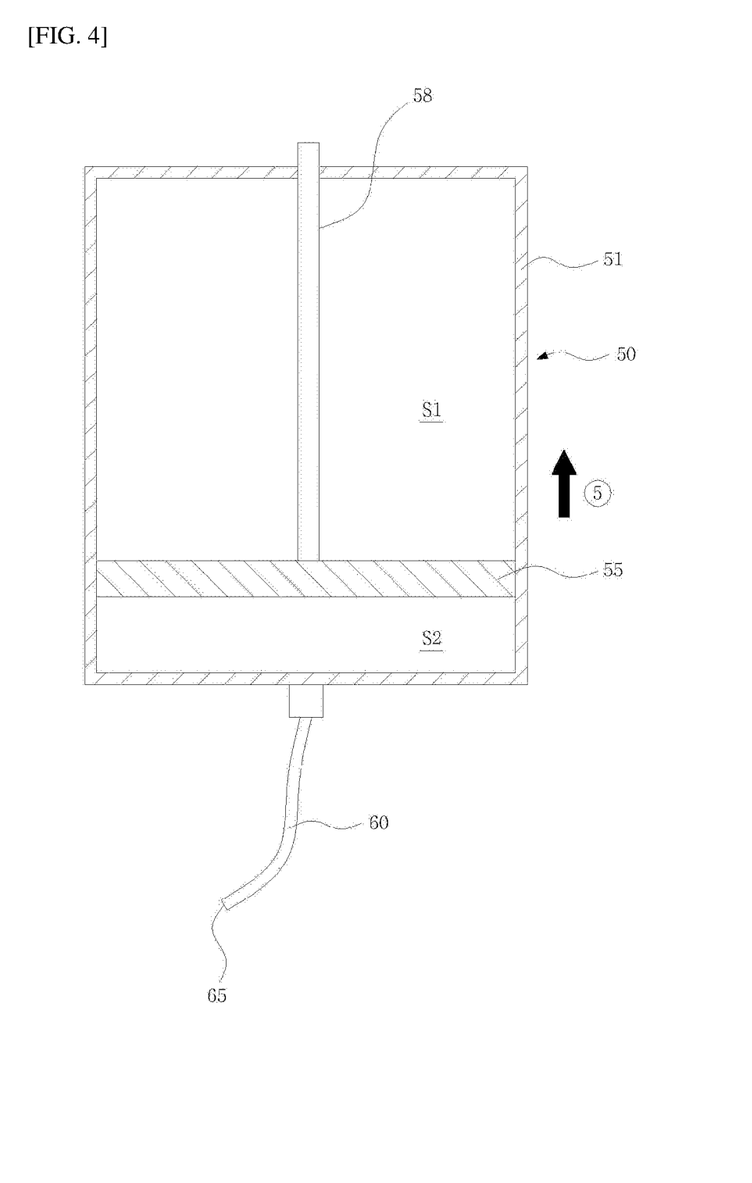
FIG. 4 is a plan view illustrating an internal structure of a negative pressure cylinder which configures an exemplary embodiment of the present invention.

In the meantime, the negative pressure cylinder 50 is connected to the interworking assembly 40. The negative pressure cylinder 50 operates by the interworking assembly 40 to generate a negative pressure therein. As illustrated in FIG. 4, the negative pressure cylinder 50 includes a cylinder housing 51 which forms a frame and a piston 55 which is installed in the cylinder housing 51 to linearly move. The connecting unit 58 is connected to the piston 55 and the connecting unit 58 is connected to the wire W of the interworking assembly 40 described above, so that consequently, the piston 55 is pulled by the interworking assembly 40.

The piston 55 lowers a pressure of internal spaces S1 and S2 while moving along the internal spaces S1 and S2 of the cylinder housing 51. The piston 55 divides the internal spaces S1 and S2 into a first space S1 which is a relatively upper portion and a second space S2 to suppress the movement of air therebetween. Even though not illustrated in the drawing, a sealing member having an elastic material such as silicon or rubber may be provided on the outer surface of the piston 55. As the piston 55 is upwardly pulled, the pressure is lowered so that the second space S2 divided by the piston 55 generates the negative pressure.

A negative pressure tube 60 is coupled to an inlet of the negative pressure cylinder 50. The negative pressure tube 60 is coupled to the inlet of the negative pressure cylinder 50 to connect the second space S2 of the negative pressure cylinder 50 in which the negative pressure is generated to the outside. Therefore, the negative pressure may be provided. Desirably, the negative pressure tube 60 is exchangeably coupled to the negative pressure cylinder 50 so that when the negative pressure tube is contaminated, the user may exchange the negative pressure tube. Reference numeral 65 denotes an inlet of the negative pressure tube 60.

The negative pressure changing unit 70 is provided in the installation space 11. The negative pressure changing unit 70 interferes with the rotating unit 30 to adjust the torque of the rotating unit 30. More specifically, an interfering protrusion 77 which controls the torque by selectively locking the gear teeth 35 provided on the outer circumferential surface of the rotating unit 30 is provided to periodically generate interference while the rotating unit 30 rotates.

As illustrated in FIG. 3, a bracket 71 of the negative pressure changing unit 70 is installed and a fixed body 75 is provided in the bracket 71. The fixed body 75 is fixed to the bracket 71 and the interfering protrusion 77 gets in and out from the fixed body 75. The interfering protrusion 77 is provided to be movable to an outer circumferential direction of the rotating unit 30 and an elastic member (not illustrated) which elastically supports the interfering protrusion 77 to the outer circumferential direction of the rotating unit 30 is provided in the negative pressure changing unit 70. By doing this, the interfering protrusion 77 moves to the outer circumferential direction of the rotating unit 30 by an elastic force of the elastic member so that the interfering protrusion 77 is continuously engaged with the gear teeth 35 of the rotating unit 30 to control the torque of the rotating unit 30. The elastic member may be omitted and the interfering protrusion 77 may be formed of an elastic material.

In the above exemplary embodiment, the gear teeth 35 is provided in the rotating unit 30 and the interfering protrusion 77 of the negative pressure changing unit 70 locks the gear teeth to control the torque. Unlikely, the gear teeth 35 of the rotating unit 30 may be omitted and the rotating unit 30 periodically causes the friction with the negative pressure changing unit 70 to control the torque. That is, the interfering protrusion 77 of the negative pressure changing unit 70 is in contact with the outer circumferential surface of the rotating unit 30 to cause friction, thereby controlling the torque. In this case, it may be configured such that the interfering protrusion 77 periodically causes the friction with the rotating unit 30 while the negative pressure changing unit 70 rotates.

Even though not illustrated in the drawings, an indicator may be installed in the external housing 10. The indicator is connected to any one of the static load elastic unit 20, the winder 43 of the interlocking assembly 40, the wire W, and the connecting unit 58 which perform the rotating operation to rotate or linearly move to identify from the outside how much the present invention is operated. That is, the indicator may indicate a remaining amount of a total amount of negative pressure which may be generated by the negative pressure generating device according to the present invention.

Even though not illustrated in the drawings, a switch may be installed in the external housing 10. The switch is a kind of a stopper and functions to selectively stop the operation of the present invention. For example, the switch locks one side of the rotating unit 30 to stop the rotation of the rotating unit 30. By doing this, before manipulating the switch, the rotating unit 30 does not rotate so that the negative pressure is not generated.

Hereinafter, an operating process by the present invention will be described.

First, the steel strip 25 of the static load elastic unit 20 is unfolded while overcoming the elastic force so that one end thereof is fixed to the rotary body 32 of the rotating unit 30. In this state, when the user manipulates the switch, the present invention operates.

For example, when the switch is turned on, the steel strip 25 of the static load elastic unit 20 is gradually wound around the first drum 21 of the static load elastic unit 20 with a predetermined force. A winding direction of the steel strip 25 is denoted by an arrow 1 of FIG. 1. As the steel strip 25 is gradually wound, the rotating unit 30 rotates in a direction of an arrow 2.

When the rotating unit 30 rotates, the winder 43 of the interlocking assembly 40 is wound coaxially with the rotary shaft 37 of the rotating unit 30. The winder 43 is wound in the direction of the arrow 3 of FIG. 2 and in this process, the wire W is wound around the winder 43. The winding direction of the wire W is represented by an arrow 4 of FIG. 2.

When the wire W is wound, the connecting unit 58 of the negative pressure cylinder 50 connected to the wire W also moves along the wire W and the connecting unit 58 pulls the piston 55 in the direction of an arrow 5 of FIG. 4. Therefore, a volume of the first space S1 between the internal spaces S1 and S2 of the negative pressure cylinder 50 is reduced and a volume of the second space S2 is increased so that the pressure of the second space S2 is reduced to generate a negative pressure. The negative pressure is provided to the outside by the negative pressure tube 60.

In the meantime, during the process of rotating the rotating unit 30, the negative pressure changing unit 70 periodically changes the torque of the rotating unit 30 to adjust the negative pressure generated in the negative pressure cylinder 50. More specifically, the interfering protrusion 77 of the negative pressure changing unit 70 selectively locks the gear teeth 35 provided on the outer circumferential surface of the rotating unit 30 to change the magnitude of the negative pressure while controlling the torque.

In this case, the interfering protrusion 77 moves to the outer circumferential direction of the rotating unit 30 by an elastic force of the elastic member so that the interfering protrusion 77 is continuously engaged with the gear teeth 35 of the rotating unit 30 to control the torque of the rotating unit 30. However, the negative pressure may vary by changing a pitch of the gear teeth 35.

As described above, the gear teeth 35 of the rotating unit 30 is omitted and the rotating unit 30 periodically causes friction with the negative pressure changing unit 70 to control the torque. In this case, the interfering protrusion 77 of the negative pressure changing unit 70 is in contact with the outer circumferential surface of the rotating unit 30 to cause friction, thereby controlling the torque.

The rotating unit 30 gradually rotates by the static load elastic unit 20 and the negative pressure is consistently generated from the negative pressure cylinder 50 during this process. In this case, since the diameter of the rotating unit 30 is larger than the winder 43 of the interlocking assembly 40, a length of the connecting unit 58 of the negative pressure cylinder 50 which is pulled is reduced and the negative pressure may be slowly generated for a long time.

In the meantime, when the negative pressure generating device described in the present exemplary embodiment is used as an automatic negative pressure wound therapy device having a pressure changing function, the negative pressure generating device may be used to be disposable, but may also be reused. For example, only components which are exposed to the outside or contaminated are exchanged and the remaining components may be reused.

Further, the negative pressure changing unit 70 which configures the exemplary embodiment of the present invention may be omitted. For example, when the pressure changing function is not necessary, the negative pressure changing unit 70 is not necessary too. Therefore, the negative pressure changing unit 70 may be omitted. In this case, the negative pressure changing unit 70 may be manufactured to be attachable to be selectively used.

It will be appreciated that various exemplary embodiments of the present invention have been described herein for purposes of illustration, and that various modifications, changes, and substitutions may be made by those skilled in the art without departing from the scope and spirit of the present invention. Accordingly, the exemplary embodiments disclosed herein are intended to not limit but describe the technical spirit of the present invention and the scope of the technical spirit of the present invention is not restricted by the exemplary embodiments. The protection scope of the present invention should be interpreted based on the following appended claims and it should be appreciated that all technical spirits included within a range equivalent thereto are included in the protection scope of the present invention.

The invention claimed is:

1. A negative pressure generating device, comprising:
a static load elastic body which provides an elastic force having a predetermined magnitude;
a rotator which is connected to the static load elastic body to rotate by the static load elastic body; and
a negative pressure cylinder which is connected to the rotator and interworks with the rotation of the rotator to generate a negative pressure therein,
wherein the rotator includes a negative pressure changer which interferes with the rotator to adjust a torque of the rotator,
wherein the negative pressure changer includes an interfering protrusion and an elastic member which elastically supports the interfering protrusion such that the interfering protrusion adjusts the torque of the rotator by engaging with gear teeth provided on an outer circumferential surface of the rotator, and
wherein the gear teeth provided on the outer circumferential surface of the rotator are continuously or discontinuously provided along the outer circumferential surface of the rotator to vary a rotating speed of the rotator.

2. The negative pressure generating device of claim 1, wherein the negative pressure cylinder includes:
a cylinder housing;
a piston which is linearly movably installed in the cylinder housing; and
a connecting unit which connects the piston and the static load elastic body.

3. The negative pressure generating device of claim 2, wherein an interlocking assembly is provided between the rotator and the negative pressure cylinder to connect to each other and the interlocking assembly is connected to the piston of the negative pressure cylinder to generate the negative pressure while pulling the piston by a torque of the rotator.

4. The negative pressure generating device of claim 3, wherein the interlocking assembly includes:
a winder which winds a wire while rotating coaxially with the rotator; and
a pulley which is installed to be adjacent to the winder and supports the wire or changes a movement path of the wire, and
one end of the wire is connected to the wire to be continuously wound and the other end is connected to the connecting unit of the negative pressure cylinder via the pulley to pull the piston.

5. The negative pressure generating device of claim 4, wherein a diameter of the rotator is larger than the winder of the interlocking assembly.

6. The negative pressure generating device of claim 1, wherein a negative pressure tube which outwardly protrudes is exchangeably coupled to an inlet of the negative pressure cylinder.

7. The negative pressure generating device of claim 1, wherein the static load elastic body is a constant torque spring which is configured such that a steel strip is wound around a drum.

8. An automatic negative pressure wound therapy device, comprising:
an external housing; and
the negative pressure generating device of claim 1 installed in the external housing.

* * * * *